(12) United States Patent
Piccolo et al.

(10) Patent No.: US 8,337,871 B2
(45) Date of Patent: Dec. 25, 2012

(54) INSECTICIDE FORMULATION

(75) Inventors: Oreste Piccolo, Sirtori (IT); Giovanna Delogu, Sassari (IT); Valerio Borzatta, Bologna (IT)

(73) Assignee: Endura S.p.A., Bolgna (IT)

( * ) Notice: Subject to any disclaimer, the term of this patent is extended or adjusted under 35 U.S.C. 154(b) by 1190 days.

(21) Appl. No.: 10/577,409

(22) PCT Filed: Oct. 26, 2004

(86) PCT No.: PCT/EP2004/052665
§ 371 (c)(1),
(2), (4) Date: Apr. 25, 2006

(87) PCT Pub. No.: WO2005/039287
PCT Pub. Date: May 6, 2005

(65) Prior Publication Data
US 2007/0072827 A1    Mar. 29, 2007

(30) Foreign Application Priority Data
Oct. 27, 2003 (IT) .............................. MI2003A2088

(51) Int. Cl.
*A01N 25/10* (2006.01)
*A01N 25/22* (2006.01)
*A01N 43/30* (2006.01)
*A01N 43/90* (2006.01)
*A01N 43/04* (2006.01)
*A01N 53/00* (2006.01)
*A01N 53/02* (2006.01)
*A01N 65/00* (2009.01)
*A61K 31/497* (2006.01)

(52) U.S. Cl. .............. 424/405; 514/58; 514/65; 514/67; 514/254.07; 514/254.1; 514/464; 514/531

(58) Field of Classification Search .................. 424/405; 514/254.07, 58, 65
See application file for complete search history.

(56) References Cited

U.S. PATENT DOCUMENTS
3,846,551 A * 11/1974 Mifune et al. .................. 514/58
4,524,068 A * 6/1985 Szejtli et al. .................... 514/58

OTHER PUBLICATIONS

R. Biebel, E. Rametzhofer, H. Klapal, D. Polheim and H. Viernstein, "Action of pyrethrum-based formulations against grain weevils", International Journal of Pharmaceutics, 2003, 256, 175-181.*
Gunning et al., "Inhibition of Resistance-related Esterases by Piperonyl Butoxide in *Helicoverpa armigera* (Lepidoptera: Noctuidae) and *Aphis gossypii* (Hemiptera: Aphididae)," Piperonyl Butoxide, The Insecticide Synergist, Edited by Denys Glynne Jones, Chapter 13, pp. 215-225, 1998.
Gunning et al., "Pyrethroid Resistance in *Heliothis armiger* (Hubner) (Lepidoptera: Noctuidae) in Australia," Journal of Economic Entomology, vol. 77, No. 5, Oct. 1984.
Szente et al., "Cyclodextrins in Pesticides," Cyclolab, Budapest, Hungary, 17, pp. 503-514.

* cited by examiner

*Primary Examiner* — John Pak
*Assistant Examiner* — Nathan W Schlientz
(74) *Attorney, Agent, or Firm* — Abelman, Frayne & Schwab

(57) ABSTRACT

The present invention provides a new insecticide formulation based on cyclodextrin characterized in that the active substance (insecticide and/or insect growth regulator), and a compound synergistic with the active substance, are complexed simultaneously with cyclodextrin. The formulation presents as a solid or as a solid/oil composition, and is soluble or completely emulsifiable in water or in aqueous mixtures of water miscible solvents. The activity of the present formulations was found to be greater than that of a mixture of the two active components each complexed separately with cyclodextrin, for the same dose. The preparation process of said formulation and its use as an insecticide in agriculture, for veterinary use or to eliminate household insects, are further aspects of the present invention.

12 Claims, No Drawings

INSECTICIDE FORMULATION

FIELD OF THE INVENTION

The present invention relates to the field of insecticide compositions, in particular those in which the insecticidal agent is mixed with substances inhibitory to the detoxification mechanisms of insects. New compositions are described in which the effect of insecticide and synergistic substance is further enhanced by simultaneous complexing with cyclodextrin.

PRIOR ART

The problem of tolerance and resistance to pesticide activity is particularly serious and of growing importance, leading to the ever more difficult control and eradication of damaging insects in agriculture, veterinary and domestic hygiene applications. Many insects have strengthened their natural defenses and their immune and enzymatic systems against toxins with which they come into contact such that, in order to destroy them, increasing doses or the continuous use of new insecticides or insect growth inhibitors are necessary, with the resultant greater risk and damage to the whole ecosystem and food chain through to man, and consequent rising costs.

The use of substances such as piperonyl butoxide (PBO) and its analogues which are able, in synergistic combination with insecticides, to inhibit the activity of certain insect metabolic enzymes involved in detoxification and pesticide resistance processes, thus able to enhance in vitro efficacy, is known in the literature [see for example Gunning et al., "Piperonyl Butoxide", p. 215-225, Academic Press (1998)], their use in vivo having also been suggested.

In order to better demonstrate synergistic activities, particularly in cases where the insect is most resistant, treatment with the synergistic product at varying times and prior to the insecticide or a repeated insecticide treatment was proposed; pre-treatment with the synergistic compound is particularly beneficial in that subsequent exposure to the insecticide takes place on an already sensitised insect, being therefore more effective. Separate administrations however are not very practical and are economically unfavourable when compared with a single application of the two components.

Also described in the literature and in patents are formulations of insecticides and insect growth regulators in cyclodextrins (CD) [see for example L. Szente et al, "Cyclodextrins in Pesticides" in "Comprehensive Supramolecular Chemistry", p. 503-514, Elsevier (1996), U.S. Pat. No. 3,846,551]. There are many principle reasons for using such inclusion complexes: modification of the physicochemical properties of pesticides, greater stability, the increased wettability and bioavailability of poorly soluble and poorly absorbable pesticides etc.

α, β, and γ cyclodextrins are natural or semi-synthetic cyclic oligosaccharides, generally non-toxic and biodegradable; β-CD and some of its derivatives, such as the hydroxypropyl (HP-β-CD) and the sulfobutyl ether (SBE-β-CD) are particularly preferred for applications.

U.S. Pat. No. 3,846,551 states that the activity of insecticides complexed with CD is better than that of uncomplexed insecticides. However, formulations also containing simultaneously a synergistic compound have never been described. PBO has also been prepared as a complex with CD (U.S. Pat. No. 4,524,068), shown to be more effective as an insecticide synergist than uncomplexed PBO; again in this case, however, the tests were carried out on mixtures of uncomplexed insecticide and PBO/CD and not on a single formulation.

The present invention proposes to overcome the drawbacks of the known art and to improve significantly the performances of commercially known insecticides or insect growth regulators by means of a single treatment; a further aspect of the invention is to obtain an economical, industrial scale preparation process for said formulation, with low or no toxicity to users.

SUMMARY

The present invention relates to a new formulation characterised by the simultaneous presence, as a complex with cyclodextrin, of
(i) an active principle being a component with insecticidal activity and/or a component with insect growth regulator activity and
(ii) a component able to synergistically enhance the activity of the active principle.

The invention also refers to the preparation of said formulation and its use in agriculture, in veterinary practise and for eliminating household insects. The formulation is obtained by subjecting both the insecticide and the synergistic compound jointly to complexing with CD.

The aforesaid formulation is also effective in cases where an insect is tolerant and resistant to insecticidal activity or to growth regulation by the same active substance, giving rise, as an insecticide and for the same dose, to an insect mortality substantially greater than that demonstrated by the same active components used in mixtures as such or complexed separately with cyclodextrin.

DETAILED DESCRIPTION OF THE INVENTION

Any cyclodextrin can be used for the purposes of the present invention. For example the cyclodextrin can be α, β, or γ cyclodextrin as such or, if appropriate, derivatised to increase the hydrophilic or hydrophobic nature thereof. Particularly preferred are β-CD, γ-CD and HP-β-CD, β-CD being more preferred due to its lower cost. The insecticides which can be used in the present invention preferably contain within their structure at least one aromatic carbocycle or heterocycle. Particularly preferred are those of pyrethroid structure such as Allethrin, Bioallethrin, Tetramethrin, Prallethrin, Cypermethrins (α-Cypermethrin, β-Cypermethrin, ξ-Cypermethrin), Esbiothrin, Permethrin, Fenpropathrin, Transfluthrin, Bifenthrin, Resmethrin, Bioresmethrin, Fenvalerate, Esfenvalerate, Tetramethrin, Imiprothrin, Phenothrin, β-Cyfluthrin, Deltamethrin, Cyhalothrin, Etofenprox, Silafluofen etc., and their enantiomeric and/or diastereoisomeric mixtures. Cypermethrin, Fenvalerate, Deltamethrin and β-Cyfluthrin and their enantiomeric and/or diastereoisomeric mixtures are most preferred.

The quantity of insecticide relative to cyclodextrin is preferably between 5% and 40% (weight/weight) and even more preferably between 10% and 25%.

Suitable insect growth regulators include, for example, Brevioxime, Buprofezin Ketoconazole, Teflubenzuron.

The quantity of growth regulator relative to cyclodextrin is preferably between 0.01% and 5% (weight/weight) and even more preferably between 0.5% and 3%.

The components able to synergistically enhance the activity of the active principle (here referred to in brief as "synergistic compounds") are per se known and already in use. Such products are inhibitors of insect detoxifying enzymes, for example esterases and oxidases. Preferred examples of synergistic compounds are piperonylbutoxide and sesamol. Piperonylbutoxide is particularly preferred. The synergistic compounds can be used as such or already preformulated with additives; one example of a commercially available preformulation is known as PB80EC-NF; it contains 88% PBO and 12% emulsifier (dodecylbenzenesulfonate, also known as SOITEM).

The quantity of synergistic compound relative to cyclodextrin is preferably between 10% and 100% (weight/weight) and even more preferably between 25% and 95%; these percentages refer to the quantity of pure synergistic compound, hence excluding additives that may be present in the preformulation.

The quantity of insecticide relative to the synergistic compound is preferably between 5% and 50% (weight/weight) and even more preferably between 10% and 30%.

Emulsifiers, UV stabilisers, antioxidants and other additives which are not particular to insecticidal activity but are useful for the specific application, can also be present in the aforesaid formulation.

The quantity of said additives relative to cyclodextrin is preferably between 0 and 30% (weight/weight) and even more preferably between 5% and 15%. These percentages refer to all additives present, including those already present in the preformulations of the active principles used.

Emulsifiers which can be used are, for example, the aforementioned dodecylbenzene-sulfate, lignosulfonates, phospholipids and polyethylene glycols.

UV stabilisers which can be used are for example 2-hydroxy-4-methoxybenzophenone, 2-hydroxy-4-octoxy-benzophenone and 4-hydroxy-2,2,6,6-tetramethylpiperidine sebacate.

Antioxidants which can be used are for example 2,6-ditert-butyl-1-hydroxy-toluene.

The composition of the invention is formulated preferably as a solid or as a solid/oil composition; said formulations can be used as such, or previously dissolved/emulsified in water or in aqueous solutions of water miscible solvents, such as a C1-4 alcohol; said aqueous solutions contain from 1% to 99% by weight, preferably from 5% to 60% by weight, of water miscible solvent.

The preparation procedure for the aforedescribed formulations is characterised by a simultaneous complexing in cyclodextrin of the synergistic compound and the insecticide and/or growth regulator.

More specifically, the procedure comprises the following passages:
(a) preparing a solution or suspension of the synergistic compound and the insecticide and/or growth regulator in a suitable solvent; the solvent is preferably an alcohol, for example ethanol or 2-propanol.
(b) preparing a solution of cyclodextrin in water or in mixtures of water/water miscible organic solvent; dissolution of the CD can be conveniently facilitated by heating (for example by maintaining it at 70° C.-90° C. for 30-90 minutes).
(c) adding the solution/suspension obtained in (a) to the solution obtained in (b);
preferably the solution/suspension in (a) is added slowly, e.g. over 2-10 hours (more preferably 4-8 hours), at a temperature of 20° C.-90° C., (more preferably 30° C.-70° C.).

Following addition of the active components, the complexing reaction goes to completion within a period generally between 12 and 36 hours (preferably 18-24 hours) maintaining the mixture under agitation, at a temperature between 20° C. and 90° C. (preferably 30° C.-70° C.).

The final CD complex, which includes both the synergistic compound and the insecticide and/or growth regulator, is recovered from the reaction mixture by known methods, such as filtration, drying or lyophilisation.

A further aspect of the invention is the use of the aforesaid formulations as an insecticide in agriculture, for veterinary use or to eliminate household insects. The joint complexing of insecticide and/or growth regulator and synergistic compound with cyclodextrin has surprisingly resulted in a significant increase in the effectiveness of the composition compared with a mixture of the two components complexed individually. By means of the invention an enhancement of the interaction between insecticide and synergistic compound is achieved; in comparative trials carried out by the inventors this enhancement has always been over 50%: the effect is therefore of substantial proportions.

Enhancement of activity gives rise to several industrially significant advantages: for instance by using the same amounts of active substance, synergistic compositions of greater activity can be obtained; or insecticide compositions with an effectiveness equal to known compositions can be obtained but with the use of less active substances; the use of less active substances results in a lower product cost, reduced environmental impact from the production process, as well as the final composition having a lower volume/weight, of further practical advantage to the crop spraying operator.

Therefore highly effective insecticide formulations, of lower cost than known formulations, were unexpectedly obtained with the present invention.

The following non-limiting examples are therefore useful to illustrate the invention.

EXPERIMENTAL PART

Example 1

Procedure for Preparing the Formulation and Stability Measurements

βCD (2 g) in distilled water (20 ml) is introduced at 80° C. into a 2-neck flask, equipped with cooler and nitrogen outlet. The solution is left for 1 hour at 80° C. under agitation. After this period, a 96% ethanol solution (25 ml) containing the synergistic compound and the insecticide and/or growth regulator in the required proportions, is added in portions over a 6 hour period at 65° C. The mixture is left at 70° C. under agitation for a further 21 hours, then the mixture is left to cool at room temperature under agitation and finally allowed to decant for 4 hours. The solid is filtered off and the solution dried under vacuum.

By means of the aforesaid procedure the following products were prepared:
   inclusion complex βCD-fenvalerate and PBO (*) (a white water soluble solid)
   inclusion complexes βCD-cypermethrins and PBO (*) (a white water soluble solid).

(*): the PBO was used starting from a commercial composition known as PB80EC-NF, containing 88% PBO and 12% SOITEM.

The inclusion complexes were stable in the solid phase for at least 30 days at 23° C.

Example 2

Preparation of a Formulation Based on Fenvalerate

Operating as in example 1, a formulation was prepared starting from 1.9 g βCD, 0.35 g fenvalerate and 1.6 g PB80EC-NF.

Example 3

Preparation of a Formulation Based on Cypermethrin

Operating as in example 1, a formulation was prepared starting from 1.9 g βCD, 0.35 g αcypermethrin and 1.6 g PB80EC-NF.

Example 4

Mortality Assay

In a mortality assay conducted as reported in the literature [Gunning R. V. et al., J. Econ. Entomol. 77, 1283-1287 (1984)] a cotton aphid specimen was used showing a resistance to cypermethrin at least 7000 times greater than the lethal dose (LD50). Using the formulation prepared as in example 3 at an active principle concentration of less than the LD50, complete mortality of the insect was obtained, while with traditional formulations containing the same doses of cypermethrin or with mixtures of cypermethrin and PBO encapsulated separately and at equal doses, the mortality was always <50% or even nil.

Example 5

Preparation of a Formulation Based on Cypermethrin

βCD (50 g) in distilled water (630 ml) at 75° C. was introduced into a two-neck flask provided with cooler and nitrogen outlet. The solution was maintained under stirring at 75° C. for 1 hour. Thereafter a solution of 2-propanol (790 ml) containing PBO/SOITEM (98/2, 13.4 g) and αcypermethrin (5.4 g) was added in portions at the temperature of 70-75° C. during 6 hours. The mixture was maintained under stirring at 75° C. for another 18 hours, then the mixture was allowed to cool at room temperature under stirring during 90 minutes and finally kept still for 3 hours. The solution was dried under vacuum obtaining, as dry residue, a formulation based on cypermethrin.

In such dry residue, containing 8.6% water and 2% 2-propanol, the PBO/cypermethrin ratio was comprised between 2.7 and 3 [as from GC-FID and $^1$H NMR (DMSO-d6) analysis, respectively] whereas the amount (weight/weight) of βCD was about 72% [$^1$H NMR (DMSO-d6)]

Example 6

Preparation of a Formulation Based on Bifenthrin

βCD (2 g) in distilled water (20 ml) at 75° C. was introduced into a two-neck flask provided with cooler and nitrogen outlet. The solution was maintained under stirring at 75° C. for 1 hour. Thereafter, a solution of 2-propanol (25 ml) containing PBO/SOITEM (98/2, 0.52 g) and bifenthrin (0.22 g) was added in portions at the temperature of 75° C. during 6 hours. The mixture was maintained under stirring at 75° C. for another 18 hours, then the mixture was cooled at room temperature under stirring during 2 hours and finally kept still for 3 hours. The solution was dried under vacuum, obtaining, as dry residue, a formulation based on bifenthrin.

Example 7

Preparation of a Formulation Based on Cyfluthrin

The formulation was prepared according to example 6, starting from 2 g βCD, 0.53 g PBO/SOITEM (98/2) and 0.22 g βcyfluthrin.

Example 8

Preparation of a Formulation Based on Cyhalothrin

The formulation was prepared according to example 6, starting from 5 g βCD, 1.33 g PBO/SOITEM (98/2) and 0.58 g λcyhalothrin.

Example 9

Preparation of a Formulation Based on Deltamethrin

The formulation was prepared according to example 6, starting from 5 g βCD, 1.33 g PBO/SOITEM (98/2) and 0.65 g deltamethrin.

Example 10

Preparation of a Formulation Based on Fenvalerate

The formulation was prepared according to example 6, starting from 5 g βCD, 1.33 g PBO/SOITEM (98/2) and 0.54 g fenvalerate.

In the dry residue thus obtained the PBO/fenvalerate ratio was about 4.2 [as from $^1$H NMR (DMSO-d6) analysis], whereas the βCD content (weight/weight) was about 76% [$^1$H NMR (DMSO-d6) analysis].

Example 11

Preparation of a Formulation Based on Cypermethrin

βCD (2 g) in distilled water (20 ml) at 75° C. was introduced into a two-neck flask provided with cooler and nitrogen outlet. The solution was maintained under stirring at 75° C. for 1 hour. Thereafter, a solution of 2-propanol (25 ml) containing PBO/SOITEM (96/4, 0.93 g) and αcypermethrin (0.36 g) was added in portions during 6 hours at the temperature of 70-75° C. The mixture was maintained under stirring at 75° C. for another 18 hours, then the mixture was cooled at room temperature under stirring during 2 hours and finally kept still for 3 hours. The oil phase was thus removed and the overlaying solution was dried under vacuum obtaining, as dry residue, a formulation based on cypermethrin.

Example 12

Preparation of a Formulation Based on Cypermethrin

βCD (1 g) in distilled water (20 ml) at 75° C. was introduced into a two-neck flask provided with cooler and nitrogen outlet. The solution was maintained under stirring at 75° C. for 1 hour. Thereafter the solution is cooled at 50° C., then at this temperature a solution of 2-propanol (25 ml) containing PBO/SOITEM (98/2, 0.26 g) and αcypermethrin (0.11 g) was added in portions during 6 hours. The mixture was maintained under stirring at 50° C. for another 18 hours, then the mixture was allowed to cool at room temperature under stirring during 2 hours and finally kept still for 3 hours. The solid (4%) is filtered off and the solution containing the inclusion complex is dried under vacuum obtaining, as dry residue, a formulation based on cypermethrin.

In such dry residue the PBO/cypermethrin ratio was about 4/1 [as from $^1$H NMR (DMSO-d6) analysis] whereas the amount (weight/weight) of βCD was about 73% [$^1$H NMR (DMSO-d6) analysis].

Example 13

Preparation of a Formulation Based on Ketoconazole

The formulation was prepared according to example 6, starting from 2 g βCD, 0.53 g PBO/SOITEM (98/2) and 0.06 g ketoconazole.

Example 14

Preparation of a Formulation Based on Cypermethrin

βCD (1 g) in distilled water (20 ml) at 75° C. was introduced into a two-neck flask provided with cooler and nitrogen outlet. The solution was maintained under stirring at 75° C. for 1 hour. Thereafter, the solution was cooled at 50° C.; then, at this temperature, a solution of 2-propanol (50 ml) containing PBO/SOITEM (98/2, 0.26 g) and αcypermethrin (0.11 g) was added in portions during 6 hours. The mixture was maintained under stirring at 50° C. for another 90 minutes, then the mixture was cooled at room temperature under stirring during 90 minutes and finally kept still for 1 hour. The separated solution was dried under vacuum obtaining, as dry residue, a formulation based on cypermethrin.

Example 15

Preparation of a Formulation Based on Pyrethrum Extracts

βCD (2 g) in distilled water (20 ml) at 75° C. was introduced into a two-neck flask provided with cooler and nitrogen outlet. The solution was maintained under stirring at 75° C. for 1 hour. Thereafter, a solution of 2-propanol (25 ml) containing PBO/SOITEM (98/2, 0.53 g) and the pyrethrum extracts at 25% w/w (0.70 g) was added in portions during 6 hours at the temperature of 70-75° C. The mixture was maintained under stirring at 75° C. for another 18 hours, then the mixture was cooled at room temperature under stirring during 2 hours and finally kept still for 3 hours. The solid was filtered off, and the overlaying solution was dried under vacuum obtaining, as dry residue, a formulation based on pyrethrum extracts.

Example 16

Preparation of a Formulation Based on Cypermethrin

βCD (5 g) in distilled water (50 ml) at 75° C. was introduced into a two-neck flask provided with cooler and nitrogen outlet. The solution was maintained under stirring at 80° C. for 1 hour. Thereafter a solution of 2-propanol (63 ml) containing PBO/SOITEM (98/2, 2.24 g) and αcypermethrin (0.91 g) was added in portions at the temperature of 75° C. during 6 hours. The mixture was maintained under stirring at 75° C. for another 18 hours, then the mixture was allowed to cool at room temperature under stirring during 2 hours and finally kept still for 3 hours. The oil phase was removed and the overlaying solution was dried under vacuum obtaining, as dry residue, a formulation based on cypermethrin.

In such dry residue the PBO/cypermethrin ratio was about 11 [as from $^1$H NMR (DMSO-d6) analysis] whereas the amount (weight/weight) of βCD was about 75% [$^1$H NMR (DMSO-d6)].

Example 17

Preparation of a Formulation Based on Cypermethrin

βCD (50 g) in distilled water (500 ml) at 75° C. was introduced into a two-neck flask provided with cooler and nitrogen outlet. The solution was maintained under stirring at 75° C. for 1 hour. Thereafter a solution of 96% ethanol (625 ml) containing PB80EC-N F (42.7 g) and αcypermethrin (9.15 g) was added in portions at the temperature of 70-75° C. during 6 hours. The mixture was maintained under stirring at 70° C. for another 18 hours, then the mixture was allowed to cool at room temperature under stirring during 2 hours and finally kept still for 3 hours. The oil phase was removed and the overlaying solution was dried under vacuum obtaining, as dry residue, a formulation based on cypermethrin.

In such dry residue the PBO/cypermethrin ratio was about 2.8 [as from $^1$H NMR (DMSO-d6) analysis] whereas the amount (weight/weight) of βCD was about 60% [$^1$H NMR (DMSO-d6)].

Example 18

Mortality Assay

A mortality assay was performed as reported in example 4 on a *Bemisia Tabaci* strain (B-Biotype) (Silver leaf whitefly) using the formulation described in example 16, dissolved in 10 ml Agral 90. The results are shown in table 1. Data obtained with αcypermethrin dissolved in 10 ml Agral 90, and with placebo (10 ml Agral 90) are shown as a reference. In all tests, concentration values are referred to the amount of active principle.

TABLE 1

| Product | Concentration (% w/v) | No. insects alive/ no. total insects after 48 hours | Mortality % |
| --- | --- | --- | --- |
| Formulation ex. 16 | 0.1 | 0/60 | 100 |
| Formulation ex. 16 | 0.01 | 0/14 | 100 |
| Formulation ex. 16 | 0.001 | 0/16 | 100 |
| Formulation ex. 16 | 0.0001 | 20/22 | 9 |
| placebo | — | 31/31 | 0 |
| αcypermethrin | 0.1 | 4/12 | 67 |
| αcypermethrin | 0.01 | 22/27 | 19 |

Example 19

Mortality Assay

A mortality assay was performed as reported in example 4 on a cotton aphid strain (*Aphis Gossypii*) using the formulation described in example 10, dissolved in 10 ml Agral 90. The results are shown in table 2. Data obtained with fenvalerate dissolved in 10 ml Agral 90, and with placebo (10 ml Agral 90) are shown as a reference. In all tests, concentration values are referred to the amount of active principle.

TABLE 2

| Product | Concentration (% w/v) | No. insects alive/ no. total insects after 24 hours | Mortality % |
| --- | --- | --- | --- |
| Formulation ex. 10 | 0.2 | 0/10 | 100 |
| Formulation ex. 10 | 0.067 | 0/10 | 100 |

TABLE 2-continued

| Product | Concentration (% w/v) | No. insects alive/ no. total insects after 24 hours | Mortality % |
|---|---|---|---|
| Formulation ex. 10 | 0.02 | 2/10 | 80 |
| Formulation ex. 10 | 0.002 | 3/10 | 70 |
| placebo | — | 10/10 | 0 |
| fenvalerate | 0.2 | 6/10 | 40 |
| fenvalerate | 0.02 | 8/10 | 20 |
| fenvalerate | 0.002 | 10/10 | 0 |

Example 20

Mortality Assay

A mortality assay was performed as reported in example 4 on a *Heicoverpa Armigera* strain (Cotton Bollworm) using the formulation described in example 17, dissolved in 10 ml Agral 90. The results are shown in table 3. Data obtained with αcypermethrin dissolved in 10 ml Agral 90, and with a mixture of αcypermethrin/PBO dissolved in 10 ml of Agral 90 (the PBO content being 0.2% with respect to αcypermethrin) are shown as a reference. In all tests, concentration values are referred to the amount of active principle.

TABLE 3

| Product | Concentration (% w/v) | No. insects alive/ no. total insects after 24 hours | Mortality % |
|---|---|---|---|
| Formulation ex. 17 | 0.001 | 0/10 | 100 |
| Formulation ex. 17 | 0.0005 | 0/10 | 100 |
| αcypermethrin | 0.001 | 4/10 | 60 |
| αcypermethrin | 0.0005 | 6/10 | 40 |
| αcypermethrin/PBO | 0.001 | 1/10 | 90 |
| αcypermethrin/PBO | 0.0005 | 3/10 | 70 |

The invention claimed is:

1. A cyclodextrin inclusion complex comprising:
   (i) an active principle being a component with insecticidal activity belonging to the pyrethroid class and/or ketoconazole; and
   (ii) piperonyl butoxide;
   wherein both components (i) and (ii) are jointly complexed within cyclodextrin.

2. The cyclodextrin inclusion complex as claimed in claim 1, wherein the cyclodextrin is selected from the group consisting of α, β, γ cyclodextrin, HP-β-cyclodextrin and SBE-β-cyclodextrin.

3. The cyclodextrin inclusion complex as claimed in claim 1, wherein the quantity of insecticide relative to cyclodextrin is between 5% and 40% (weight/weight).

4. The cyclodextrin inclusion complex as claimed in claim 1, wherein the quantity of ketoconazole relative to cyclodextrin is between 0.01% and 5% (weight/weight).

5. The cyclodextrin inclusion complex as claimed in claim 1, wherein the quantity of component (ii) relative to cyclodextrin is between 10% and 100% (weight/weight).

6. The cyclodextrin inclusion complex as claimed in claim 1, wherein the quantity of insecticide relative to the component (ii) is between 5% and 50% (weight/weight).

7. The cyclodextrin inclusion complex as claimed in claim 1, formulated for use in solid form or as a solid/oil composition, dissolved/emulsified in water or in aqueous solutions for water miscible solvents.

8. A composition comprising the cyclodextrin inclusion complex as claimed in claim 1, further comprising emulsifiers, UV stabilizers, antioxidants and other additives in a quantity between 0 and 30% (weight/weight).

9. Process for preparing the cyclodextrin inclusion complex as claimed in claim 1, characterized by simultaneously complexing the component (ii) and the component (i).

10. Process as claimed in claim 9, comprising the following steps:
    (a) preparing a solution or suspension of the component (ii) and the component (i) in a suitable solvent;
    (b) preparing a solution of cyclodextrin in water or in aqueous mixtures of water miscible organic solvents; and
    (c) adding the solution/suspension obtained in (a) to the solution obtained in (b).

11. A method to eliminate household insects, or an insecticide method in agriculture, which comprises applying to the surface to be treated, a cyclodextrin inclusion complex according to claim 1.

12. A veterinary insecticide method which comprises applying to an animal in need, a cyclodextrin inclusion complex according to claim 1.

* * * * *